United States Patent [19]

Cabri et al.

[11] Patent Number: 5,399,679
[45] Date of Patent: Mar. 21, 1995

[54] (1′R,3S,4R)4-ACYLTHIO AZETIDINONES

[75] Inventors: Walter Cabri, Rozzano; Ilaria Candiani, Busto Arsizio; Franco Zarini, Settimo Milanese Milano; Angelo Bedeschi, Milan, all of Italy

[73] Assignee: Farmitalia Carlo Erba S.r.l., Milan, Italy

[21] Appl. No.: 54,233

[22] Filed: Apr. 30, 1993

[30] Foreign Application Priority Data

Jun. 16, 1992 [GB] United Kingdom ............... 9212707
Dec. 17, 1992 [GB] United Kingdom ............... 9226292

[51] Int. Cl.⁶ ............... C07D 499/00; A61K 31/425
[52] U.S. Cl. ............................... 540/310; 540/358
[58] Field of Search .................. 540/200, 310, 358

[56] References Cited

U.S. PATENT DOCUMENTS

| | | | |
|---|---|---|---|
| 4,631,150 | 12/1986 | Battistini et al. | 540/310 |
| 4,782,145 | 11/1988 | Brighty | 540/310 |
| 4,952,577 | 8/1990 | Alpegiani et al. | 514/192 |
| 4,962,196 | 10/1990 | Hungerbühler et al. | 540/337 |

FOREIGN PATENT DOCUMENTS 0295100 12/1988 European Pat. Off.
WO91/14691 10/1991 WIPO.

OTHER PUBLICATIONS

Tetrahedron Letters, vol. 35, No. 20, pp. 3379–3382, 1994.

*Primary Examiner*—Nicholas Rizzo
*Attorney, Agent, or Firm*—Oblon, Spivak, McClelland, Maier & Neustadt

[57] ABSTRACT

There is provided a process for preparing a compound of formula (I)

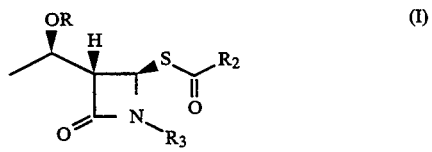

wherein R is H or a hydroxy protecting group, $R_2$ is an organic residue and $R_3$ is H or a nitrogen protecting group, which process comprises reacting together a compound of formula (II)

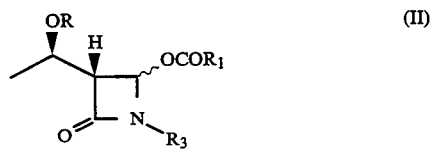

wherein $R_1$ is a $C_1$–$C_4$ alkyl or a phenyl group, R and $R_3$ are as defined above, a compound of formula (III)

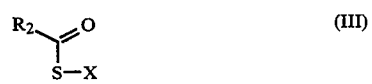

wherein $R_2$ is as defined above and X is a cation or a silicon-containing residue, and a salt of a group IIa, IIb or transition element. The compounds of formula (I) are intermediates in the synthesis of penem antibiotics.

11 Claims, No Drawings

(1'R,3S,4R)4-ACYLTHIO AZETIDINONES

The present relates to a new method for synthesis of (1'R,3S,4R)4-acylthio azetidinones from 4-acetoxy azetidinones.

It is known that 4-acylthio azetidinones are key intermediates in the synthesis of many useful penem antibiotics, see our U.S. Pat. Nos. 4,631,150 and 4,952,577.

These important intermediates are usually prepared from 4-acetoxy azetidinones by reaction with a suitable thioacid in an aqueous or organic-aqueous medium in the presence of a base, but this methodology is often unsuitable, especially when sensitive thioacids are used. Moreover high amount of impurities are often present in the above conditions, and therefore an additional chromatographic purification step is needed. The present invention relates to a procedure which provides mild conditions necessary for sensitive thioacids and gives high yield (up to 95%) of the desidered thioesters with the desidered correct configuration with only negligible amount of by-product. Moreover this procedure is general and gives high yields with a wide range of thioacids in mild and safe conditions.

The present invention provides a process for preparing a compound of formula (I)

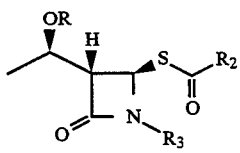

wherein R is H or a hydroxy protecting group, $R_2$ is:
(i) a linear, branched or cyclic $C_1$-$C_6$ alkyl group optionally substituted by one or more groups chosen from free and protected hydroxy and amino groups and alkoxy, thioalkyl, acyloxy and carbamoyloxy groups; or
(ii) a 2-pyridyl or a 2-tetrahydrofuranyl ring or an aromatic group, optionally substituted by one or more groups chosen from free and protected hydroxy and amino groups and alkoxy, acyloxy, carbamoyloxy and linear or branched $C_2$-$C_4$ alkyl groups, the alkyl groups being, in turn, optionally substituted by a free or protected hydroxy or amino group, an alkoxy, acyloxy, carbamoyloxy group, or a quaternary onium derivative with an optionally substituted heterocyclic base;

and $R_3$ is H or a nitrogen protecting group, which process comprises reacting together a compound of formula II

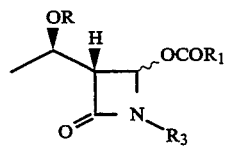

wherein $R_1$ is a linear or branched $C_1$-$C_4$ alkyl group or a phenyl group and R and $R_3$ are as defined above, a compound of formula (III)

wherein $R_2$ is as defined above and X is a cation or a silicon-containing residue, and a salt of a group IIa, IIb or transition element.

The configuration of the compounds of the formula I is 1'R,3S,4R in order to obtain the desidered final (5R,6S,1'R) stereochemistry of the penem nucleus. In one embodiment the process of the invention comprises mixing together, in an organic solvent, the compound of formula II and compound of formula III and then adding thereto the said salt.

In another embodiment the process of the invention comprises mixing together, in an organic solvent, the compound of formula III and the said salt and then adding thereto the compound of formula II.

Typically, the reaction is carried out in an organic solvent with from 1 to 5 molar equivalents, preferably from 1 to 3 molar equivalents, of the compound of the formula (III). The salt of the group IIa, IIb or transition element is typically present in an amount of from 0.1 to 5 molar equivalents, preferably from 0.1 to 3 molar equivalents. The reaction temperature is typically from −20° C. to 60° C., preferably from 0° C. to 40° C. The reaction is typically conducted for a time of from 1 hour to 3 days, preferably from 4 hours to 1 day.

A linear or branched $C_1$-$C_6$ alkyl group is typically a linear or branched $C_1$-$C_4$ alkyl group. Examples of a $C_1$-$C_4$ alkyl group are methyl, ethyl, propyl, i-propyl, butyl, sec butyl and tert butyl, in particular methyl or ethyl.

R is preferably H or a hydroxy protecting group.
$R_2$ is preferably:
(i) a linear or branched $C_1$-$C_4$ alkyl group optionally substituted by a free or protected hydroxy or amino group, or a linear, branched or cyclic $C_1$-$C_4$ alkoxy, thioalkyl or $C_1$-$C_5$ alkanoyloxy group, or a carbamoyloxy group.
(ii) a 2-tetrahydrofuranyl or a 2-pyridyl group optionally substituted by one or more groups chosen from free and protected hydroxy and amino groups and alkoxy and acyloxy groups.
(iii) a phenyl ring optionally substituted by one or more groups chosen from:
a free or protected hydroxy group, a $C_1$-$C_4$ alkyl group which is optionally substituted by a free or protected hydroxy or amino group or a quaternary onium derivative with an optionally substituted heterocyclic base. Examples of suitable quaternary onium derivatives include pyrrolidinium and pyridinium groups.

When $R_2$ is a substituted linear or branched $C_1$-$C_4$ alkyl group the substituent is most preferably selected from a carbamoyloxy, acetoxy, methoxy, free or protected hydroxy, and free or protected amino group. When $R_2$ is an optionally substituted 2-pyridyl group it is preferably an unsubstituted 2-pyridyl group or a 2-pyridyl group substituted by one or more free or protected hydroxy groups. When $R_2$ is an unsubstituted 2-tetrahydrofuranyl group, the asymetric carbon atom has R configuration.

Particularly preferred $R_2$ groups are carbamoyloxymethyl, acetoxymethyl, methoxymethyl, free or protected hydroxymethyl, 2-tetrahydrofuranyl and free or protected aminomethyl groups. When $R_3$ is a nitrogen protecting group it is preferably chosen from t-butyldimethyl, trimethylsilyl $C_1$–$C_4$ alkyl and triethylsilyl groups.

When the hydroxy or amino groups referred to herein are protected, they may be protected by any group known to be suitable for protecting the hydroxy or amino moiety. Preferably the protecting group is chosen from t-butyldimethylsilyl, trimethylsilyl, triethylsilyl, pyranyl, acyl, p-nitrobenzyloxycarbonyl and 2,2,2-trichloroethoxycarbonyl groups.

When the X group represents a cation it is preferably an alkali or alkaline-earth metal cation, an ammonium cation or a tri- or tetra-alkylammonium cation. Preferably, X is a sodium, potassium or trialkylammonium cation.

X acts as an activating residue, giving a reactive form of the compound of formula (III) which can then replace the group —$OCOR_1$ in the compound of formula (II). When X is a silicon-containing residue, it is typically a group —$SiR'R''R'''$ wherein each of R', R" and R''' is, independently, a linear or branched $C_1$–$C_4$ alkyl group. Preferred examples of $SiR'R''R'''$ are a trimethylsilyl and a t-butyldimethylsilyl group.

Preferably the salt of a group IIa, IIb or transition element is a halogenide, such as a chloride, bromide or iodide, or a carboxylate, such as an acetate, or a salt with an inorganic anion, such as a carbonate. A group IIa element is preferably Mg and a group IIb element is preferably Zn.

The transition element is a first-, second- or third-row transition element, typically a first-row transition element. Preferably it is selected from Fe, Co and Ni. The salt of a transition element is preferably an iron trihalogenide such as $FeCl_3$, $FeBr_3$ and $FeI_3$.

Suitable organic solvents include polar solvents, such as acetonitrile, tetrahydrofuran, dioxane, dimethoxyethane, ethyl acetate and mixtures thereof. Preferred solvents are dioxane, tetrahydrofuran, dimethoxyethane and ethyl acetate.

The salt of the group IIa, IIb or transition element may be, if desired, recycled by removal them from the reaction media by usual methods, such as filtration or water extraction, and then recovering the starting salt.

Optionally the said salt may be used in catalytic amounts (e.g. 10 to 20% by mole of the starting material), provided that a suitable silicon derivative of the abovesaid thioacid is used, i.e. provided X in formula (III) is a silicon-containing residue.

Optionally a complex may be formed in situ, mixing together the compound of formula (III) and the said salt in an organic solvent, and reacted with a compound of formula (II).

The starting compounds of the formula (II) are known compounds and some are commercially available.

Two isomers, namely 1'R,3R,4R, and 1'R, 3R, 4S of the compounds of the formula II may be present and the two isomers or their mixture may be used as starting materials.

The compounds of formula (III) are known or may be prepared by known methods.

Due to low cost of the reagent and to high yields, and easy and mild reaction conditions the process of the invention is paricularly useful for the preparation of compounds of formula (I) on a large scale.

As stated above, the compounds of the formula (I) are key intermediates in the synthesis of many useful penem antibiotics. The process of the invention may therefore be particularly useful in the industrial production of penem antibiotics.

In one embodiment, the process of the invention includes the additional step of converting the compound of formula (I) into a penem antibiotic. For example the penem antibiotic produced may be a compound of the following formula (Ia):

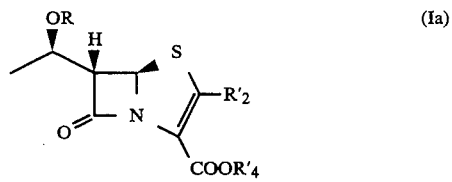

wherein $R'_2$ is carbamoyloxymethyl, methoxymethyl or 2(R)tetrahydrofuranyl group and $R'_4$ is a hydrogen atom, an acetoxymethyl or (5-methyl-2-oxo-1,3 dioxolen-3-yl)methyl group, or a pharmaceutically acceptable salt thereof.

The conversion of a compound of formula (I) into a penem antiobiotic, such a compound of formula (Ia), is carried out by performing conventional reactions well known in the chemistry of penem compounds. The conversion typically comprises cyclization and removal of the optionally present protecting groups.

it may further include an optional optical resolution or the introduction of a substituent to form an ester group at position 3 of the penem nucleus, for example the introduction of the group $R'_4$ in formula (Ia) defined above.

The resulting penem antibiotic, for example a compound of formula (Ia), may then, if desired, be converted into a pharmaceutically acceptable salt thereof.

The penem antibiotic, such as a compound of formula (Ia) or a pharmaceutically acceptable salt thereof, may then be formulated together with a pharmaceutically acceptable carrier or diluent. The resulting pharmaceutical composition may be for oral or parenteral administration.

The following examples further illustrate the process of the invention.

EXAMPLE 1

4(R)-carbamoyloxyacetylthio-3(S)-[1(R)t-butyldimethylsilyloxyethyl]azetidin-2-one To a solution of 4-(R)acetoxy-3(R)-[1(R)t-butyldimethylsilyloxyethyl]azetidin-2-one (2.87 g) in dioxane (40 ml) the potassium salt of carbamoyloxythioacetic acid (2.1 g) was added. Zinc bromide (2.7 g) was added to the resulting suspension and the reaction mixture was stirred for 4 hours at 40° C. The reaction mixture was then cooled at room temperature and poured in a mixture of ethyl acetate and water. The organic layer was separated, washed twice with water, dried over anhydrous sodium sulfate, and evaporated in vacuo. The solid residue was taken-up with $CH_2Cl_2$. Upon addition of hexanes and cooling a white solid was precipitated, and collected by filtration to give 3.26 g of the title product (90% yield).

NMR ($CDCl_3$) δ (ppm): 0.1 (6H, s); 0.75 (9H, s); 1.18 (3H, d); 3.18 (1H, dd); 4.23 (1H, m); 4.75 (2H, ABq); 5.35 (1H, d); 5.45 (2H, br s); 7.05 (1H, s)

EXAMPLE 2

4(R)-carbamoyloxyacetylthio-3(S)-[1(R)t-butyldimethylsilyloxyethyl]azetidin-2-one The reaction was carried out as described in example 1, except that ethyl acetate was used as solvent. After 3 hours the reaction was cooled and, after the usual work-up and crystallization the title product was obtained in 85% yield.

EXAMPLE 3

4(R)-carbamoyloxyacetylthio-3(S)-[1(R)t-butyldimethylsilyloxyethyl]azetidin-2-one The reaction was carried out as described in example 1, except that the reaction was run at room temperature for 8 hours. After the usual work-up and crystallization the title product was obtained in 90% yield.

EXAMPLE 4

4(R)-carbamoyloxyacetylthio-3(S)-[1(R)t-butyldimethylsilyloxyethyl]azetidin-2-one The reaction was carried out as described in the previous examples, except that zinc chloride was used instead. After the usual work-up and crystallization the title product was obtained in 75–80% yield.

EXAMPLE 5

4(R)-carbamoyloxyacetylthio-3(S)-[1(R)t-butyldimethylsilyloxyethyl]azetidin-2-one The reaction was carried out as described in the previous examples, except that magnesium chloride was used instead. After the usual work-up and crystallization the title product was obtained in about 50% yield.

EXAMPLE 6

4(R)-carbamoyloxyacetylthio-3(S)-[1(R)t-butyldimethylsilyloxyethyl]azetidin-2-one The reaction was carried out as described in the previous examples, except that iron trichloride (1.5 equivalents) was used instead. After the usual work-up and crystallization the title product was obtained in 60% yield.

EXAMPLE 7

4(R)-carbamoyloxyacetylthio-3(S)-[1(R)t-butyldimethylsilyloxyethyl]azetidin-2-one The reaction was carried out as described in example 1, except that 2.6 g of the starting thioacid salt and 3.4 g of zinc bromide were used instead. After 1.5 hours heating and the usual work-up and crystallization the title product was obtained in 95% yield.

EXAMPLE 8

4(R)-methoxyacetylthio-3(S)-[1(R)t-butyldimethylsilyloxyethyl]azetidin-2-one

To a solution of 4-(R)acetoxy-3(R)-[1(R)t-butyldimethylsilyloxyethyl]azetidin-2-one (2.87 g) in dioxane (40 ml) the potassium salt of methoxythioacetic acid (1.7 g) was added. Zinc bromide (2.7 g) was added to the resulting suspension and the reaction mixture was stirred for 4 hours at 40° C. The reaction mixture was then cooled at room temperature and poured in a mixture of ethyl acetate and water. The organic layer was separated, washed twice with water, dried over anhydrous sodium sulfate, and evaporated in vacuo. The residue was purified by column chromatography to give 2.99 g of the title product (90% yield). NMR (CDCl$_3$) δ (ppm): 0.1 (6H, s); 0.83 (9H, s); 1.16 (3H, d); 3.13 (1H, dd); 3.42 (3H, s), 4.01 (2H, s) 4.20 (1H, m); 5.22 (1H, d); 6.55 (1H, s)

EXAMPLE 9

4(R)-acetylthio-3(S)-[1(R)t-butyldimethylsilyloxyethyl]azetidin-2-one

To a solution of 4-(R)acetoxy-3(R)-[1(R)t-butyldimethylsilyloxyethyl]azetidin-2-one (2.87 g) in dioxane (40 ml) the sodium salt of thioacetic acid (1.2 g) was added. Zinc bromide (2.7 g) was added to the resulting suspension and the reaction mixture was stirred for 4 hours at 40° C. The reaction mixture was then cooled at room temperature and poured in a mixture of ethyl acetate and water. The organic layer was separated, washed twice with water, dried over anhydrous sodium sulfate, and evaporated in vacuo. The residue was purified by column chromatography to give 2.7 g of the title product (89% yield).

NMR (CDCl$_3$) δ (ppm): 0.1 (6H, s); 0.86 (9H, s); 1.19 (3H, d); 2.37 (3H, s); 3.14 (1H, dd); 4.24 (1H, m); 5.31 (1H, d); 6.31 (1H, s).

EXAMPLE 10

4(R)-[4-(t-butyldiphenylsilyloxymethyl)]benzoylthio-3(S)-[1(R)(t-butyldimethylsilyloxyethyl)]azetidin-2-one To a solution of 4-(R)acetoxy-3(R)-[1(R)t-butyldimethylsilyloxyethyl]azetidin-2-one (2.87 g) in dioxane (40 ml) the potassium salt of [4-(t-butyldiphenylsilyloxymethyl)]-thiobenzoic acid (4.99 g) was added. Zinc chloride (1.64 g) was added to the resulting mixture and the reaction mixture was stirred for 4 hours at 40° C. The reaction mixture was then cooled at room temperature and poured in a mixture of ethyl acetate and water. The organic layer was separated, washed twice with water, dried over anhydrous sodium sulfate, and evaporated in vacuo. The residue was purified by column chromatography to give 5.13 g of the title product (85% yield).

EXAMPLE 11

4(R)-nicotinoylthio-3(S)-[1(R)t-butyldimethylsilyloxyethyl]azetidin-2-one

To a solution of 4-(R)acetoxy-3(R)-[1(R)t-butyldimethylsilyloxyethyl]azetidin-2-one (2.87 g) in dioxane (40 ml), the sodium salt of thionicotinic acid (1.94 g) was added. Zinc chloride (1.7 g) was added to the resulting mixture and the reaction mixture was stirred for 4 hours at room temperature. The reaction mixture was then cooled at room temperature and poured in a mixture of ethyl acetate and water. The organic layer was separated, washed twice with water, dried over anhydrous sodium sulphate, and evaporated in vacuo. The residue was purified by column chromatography to give 1.9 g of the title product (52% yield).

EXAMPLE 12

4(R)-carbamoyloxyacetylthio-3(S)-[1(R)t-butyldimethylsilyloxyethyl]azetidin-2-one The reaction was carried out as described in example 8, except that the triethylammonium salt of carbamoyloxythioacetic acid (3.04 g) was used instead. After 4 hours the reaction was cooled and, after the usual work-up and crystallization the title product was obtained in 90% yield.

EXAMPLE 13

4(R)-methoxyacetylthio-3(S)-[1(R)t-butyldimethylsilyloxyethyl]azetidin-2-one The reaction was carried out as described in example 8, except that methoxythioacetic acid (1.4 g) was used instead, and triethylamine (1.82 ml) was added to the reaction mixture. After 4 hours the reaction was cooled and, after the usual work-up and crystallization the title product was obtained in 90% yield.

EXAMPLE 14

4(R)-carbamoyloxyacetylthio-3(S)-[1(R)t-butyldimethylsilyloxyethyl]azetidin-2-one The reaction was carried out as described in example 1, except that the trimethylsilyl derivative of carbamoyloxythioacetic acid (5.6 g) and 0.32 g of zinc bromide were used instead in acetonitrile. After 15 hours stirring at room temperature the reaction was worked-up as usual. The title product was obtained in 70% yield.

EXAMPLE 15

4(R)-carbamoyloxyacetylthio-3(S)-[1(R)t-butyldimethylsilyloxyethyl]azetidin-2-one The reaction was carried out as described in example 1, except that zinc iodide was used instead. After the usual work-up and crystallization the title product was obtained in 80% yield.

EXAMPLE 16

4(R)-carbamoyloxyacetylthio-3(S)-[1(R)t-butyldimethylsilyloxyethyl]azetidin-2-one The reaction was carried out as described in example 1, except for a mixture of 4(R and S) acetoxy-3(R)-[1(R)t-butyldimethylsilyloxyethyl]azetidin-2-one which was used as starting material. The title product was obtained in 88% yield.

EXAMPLE 17

4(R)-(2-tetrahydrofuranoylthio-3(S)-[1(R)t-butyldimethylsilyloxyethyl]azetidin-2-one To a solution of 4(R) acetoxy-3(R)-[1(R)t-butyldimethylsilyloxyethly]azetidin-2-one (2.87 g) in dioxane (40 ml) the potassium salt of tetrahydrofuran-2-thiocarboxylic acid (2.1 g) was added. Zinc bromide (2.7 g) was added to the resulting suspension and the reaction mixture was stirred for 6 hours at 35° C. After the usual work-up the title product was obtained in 92% yield.

MNR(CDCl$_3$) δ (ppm) 1.19 (d, 1.5 H), 1.21 (d, 1.5 H), 1.82–2.40 (m 4H), 3.15–3.20 (m, 1H), 3.90–4.13 (m,2H), 4.17–4.33 (m, 1H), 4.48 (dd, 1H), 5.18 (d, 0.5 H), 5.23 (d, 0.5 H), 6.28 (d, 1H).

We claim:

1. A process for preparing a compound of formula (I) having 1′R, 3S, 4R configuration

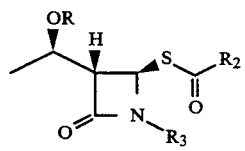

wherein R is H or a hydroxy protecting group, R$_2$ is:
(i) a linear, branched or cyclic C$_1$–C$_6$ alkyl group optionally substituted by one or more groups chosen from free and protected hydroxy and amino groups and alkoxy, thioalkyl, C$_1$–C$_5$ alkanoyloxy and carbamoyloxy groups; or (ii) a 2-pyridyl or 2-tetrahydrofuranyl ring or an aromatic group, optionally substituted by one or more groups chosen from free and protected hydroxy and amino groups and alkoxy, C$_1$–C$_5$ alkanoyloxy, carbamoyloxy and linear or branched C$_1$–C$_4$ alkyl group, the alkyl groups being, in turn, optionally substituted by a free or protected hydroxy or amino group, an alkoxy, C$_1$–C$_5$ alkanoyloxy, carbamoyloxy group, or a pyrrolidinium or pyridinium compound; wherein said hydroxy protecting group is a member selected from the group consisting of t-butyl dimethylsilyl, trimethylsilyl, triethylsilyl, pyranyl, acyl, p-nitrovinyloxycarbonyl, and 2,2,2-trichloroethoxycarbonyl; and R$_3$ is H or a nitrogen protecting group, which process comprises reacting together a compound of formula II

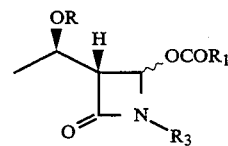

wherein R$_1$ is a linear or branched C$_1$–C$_4$ alkyl group or a phenyl group and R and R$_3$ are as defined above, with 1 to 5 molar equivalents of a compound of formula (III)

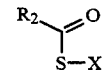

wherein R$_2$ is as defined above and X is a cation or a silicon-containing residue of formula —SiR′R″R‴ wherein each of R′, R″ and R‴ is, independently, a linear or branched C$_1$–C$_4$ alkyl group, and 0.1 to 5 molar equivalents of a salt of a group IIa, IIb or transition element, wherein said process is carried out in an organic solvent selected from the group consisting of acetonitrile, tetrahydrofuran, dioxane, dimethoxyethane, ethyl acetate and mixtures thereof.

2. A process according to claim 1 which comprises mixing together, in an organic solvent, the compound of formula II and the compound of formula III and then adding thereto the said salt.

3. A process according to claim 1 which comprises mixing together, in an organic solvent, the compound of formula III and the said salt and then adding thereto the compound of formula II.

4. A process according to any one of claims 1 to 3 in which the reaction is carried out in an organic solvent with from 1 to 5 molar equivalents of the compound of formula (III), and from 0.1 to 5 molar equivalents of the said salt, at a temperature of from −20° C. to 60° C., for a time of from 1 hour to 3 days.

5. A process according to claim 1 in which the said salt is a Zn, Mg or Fe salt.

6. A process according to claim 1 in which the salt is a halogenide, an acetate or a carbonate.

7. A process according to claim 1, in which R is H or a hydroxy protecting group; R$_2$ is (i) a linear or branched $C_1$–$C_4$ alkyl group optionally substituted by a free or protected hydroxy or amino group, a linear, branched or cyclic $C_1$–$C_4$ alkoxy, thioalkyl or $C_1$–$C_5$ alkanoyloxy group, or a carbamoyloxy group;

(ii) a 2-pyridyl or a 2-tetrahydrofuranyl group optionally substituted by one or more groups chosen from free and protected hydroxy and amino groups, and alkoxy and $C_1$–$C_5$-alkanoyloxy groups; or (iii) a phenyl ring optionally substituted by one or more groups chosen from a free or protected hydroxy group, a linear or branched $C_1$–$C_4$ alkyl group which is optionally substituted by a free or protected hydroxy or amino group, or a pyrrolidinium or pyridinium compound; and X is an alkali or alkaline-earth metal cation, an ammonium cation, a tri- or tetra-alkylammonium cation, or a trimethylsilyl or t-butyldimethylsilyl group.

8. A process according to claim 7 wherein $R_2$ is (i) a linear or branched $C_1$–$C_4$ alkyl group optionally substituted by a carbamoyloxy, acetoxy, methoxy, free or protected hydroxy, or a free or protected amino group;

(ii) an unsubstituted 2-pyridyl group or a 2-pyridyl group substituted by one or more free or protected hydroxy groups; or (iii) an unsubstituted 2-tetrahydrofuranyl group having an asymetric carbon atom in R configuration.

9. A process for preparing a compound of formula (I) having 1'R, 3S, 4R configuration

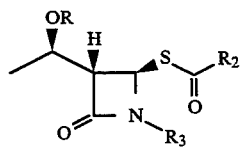

wherein R is H or a hydroxy protecting group, $R_2$ is:

(i) a linear, branched or cyclic $C_1$–$C_6$ alkyl group optionally substituted by one or more groups chosen from free and protected hydroxy and amino groups and alkoxy, thioalkyl, $C_1$–$C_5$ alkanoyloxy and carbamoyloxy groups; or (ii) a 2-pyridyl or 2-tetrahydrofuranyl ring or an aromatic group, optionally substituted by one or more groups chosen from free and protected hydroxy and amino groups and alkoxy, $C_1$–$C_5$ alkanoyloxy, carbamoyloxy and linear or branched $C_1$–$C_4$ alkyl group, the alkyl groups being, in turn, optionally substituted by a free or protected hydroxy or amino group, an alkoxy, $C_1$–$C_5$ alkanoyloxy, carbamoyloxy group, or a pyrrolidinium or pyridinium compound; wherein said hydroxy protecting group is a member selected from the group consisting of t-butyl dimethylsilyl, trimethylsilyl, triethylsilyl, pyranyl, acyl, p-nitrovinyloxycarbonyl, and 2,2,2-trichloroethoxycarbonyl; and $R_3$ is H or a nitrogen protecting group, which process comprises the steps of:

reacting together a compound of formula II

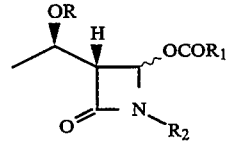

wherein $R_1$ is a linear or branched $C_1$–$C_4$ alkyl group or a phenyl group and R and $R_3$ are as defined above, with 1 to 5 molar equivalents of a compound of formula (III)

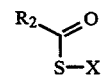

wherein $R_2$ is as defined above and X is a cation or a silicon-containing residue of formula —SiR'R''R''' wherein each of R', R'' and R''' is, independently, a linear or branched $C_1$–$C_4$ alkyl group, and 0.1 to 5 molar equivalents of a salt of a group IIa, IIb or transition element, wherein said reacting step is carried out in an organic solvent selected from the group consisting of acetonitrile, tetrahydrofuran, dioxane, dimethoxyethane, ethyl acetate and mixtures thereof; and converting the compound of formula (I) into a penem antibiotic.

10. A process according to claim 9 wherein the penem antibiotic is a compound of the following formula (Ia):

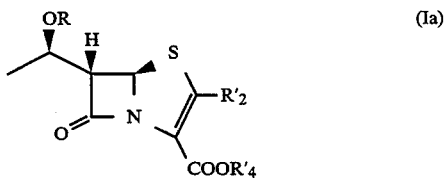

wherein $R'_2$ is a carbomoyloxymethyl, a methoxymethyl or a 2-(R)tetrahydrofuranyl group, $R'_4$ is a hydrogen atom, an acetoxymethyl or (5-methyl-oxo-1,3 dioxolen-3-yl)methyl group; or a pharmaceutically acceptable salt thereof.

11. A process according to claim 10, wherein said step of converting the compound of formula (I) into said compounds of formula (Ia) is performed by cyclization of the compound of formula (I).

* * * * *